United States Patent [19]

Lee et al.

[11] 4,371,540

[45] Feb. 1, 1983

[54] NITROIMIDAZOLES OF LOW TOXICITY AND HIGH ACTIVITY AS RADIOSENSITIZERS OF HYPOXIC TUMOR CELLS

[75] Inventors: William W. Lee, Palo Alto; J. Martin Brown, Stanford; Abelardo P. Martinez, San Jose, all of Calif.; Michael J. Cory, Chapel Hill, N.C.

[73] Assignee: The United States of America as represented by the Secretary of the Department of Health and Human Services, Washington, D.C.

[21] Appl. No.: 180,373

[22] Filed: Aug. 22, 1980

Related U.S. Application Data

[63] Continuation-in-part of Ser. No. 75,603, Sep. 14, 1979, abandoned.

[51] Int. Cl.³ .............................................. A61K 31/415
[52] U.S. Cl. .................................. 424/273 R; 548/338
[58] Field of Search ...................... 548/338; 424/273 R

[56] References Cited

U.S. PATENT DOCUMENTS 3,679,698  7/1972  Beaman et al. ...................... 548/338

OTHER PUBLICATIONS

Asquith et al., Radiation Research 1974, vol. 60, pp. 108–118.
Hall et al., British Journal of Cancer 1978, vol. 37, Suppl. III, pp. 120–123.
Dische et al., British Journal of Cancer 1977, vol. 35, pp. 567–579.
Brown et al., Radiation Research 1980, vol. 82, pp. 171–190.

*Primary Examiner*—Henry R. Jiles
*Assistant Examiner*—N. Harkaway
*Attorney, Agent, or Firm*—Holman & Stern

[57] ABSTRACT

Two compounds represented by the formula

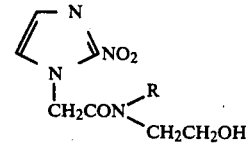

wherein R is hydrogen or a 2-hydroxyethyl radical are reported to have minimum penetration into the brain and nerve tissues combined with maximum penetration into hypoxic tumor cells. This combination of properties makes these compounds the optimal radiosensitizers among electron-affinic 1-substituted 2-nitroinidazoles.

6 Claims, 2 Drawing Figures

NITROIMIDAZOLES OF LOW TOXICITY AND HIGH ACTIVITY AS RADIOSENSITIZERS OF HYPOXIC TUMOR CELLS

DESCRIPTION

REFERENCE TO GOVERNMENT CONTRACT

The invention described herein was made in the course of or under Contract No. NO1-CM-87207 with the U.S. Dept. of Health, Education and Welfare.

CROSS REFERENCE TO RELATED APPLICATION

This application is a continuation-in-part of copending U.S. application Ser. No. 75,603 filed Sept. 14, 1979, now abandoned.

TECHNICAL FIELD

The invention relates to 2-nitroimidazoles that have improved radiosensitizing capability over 2-nitroimadazoles currently deemed suitable for clinical use to radiosensitize hypoxic cell.

BACKGROUND ART

Work has been going on for many years on methods for increasing the radiosensitivity of tumors relative to that of normal tissues. One of these methods involves administering a pharmaceutical that sensitizes the tumor cells to radiation. The use of such pharmaceuticals, called radiosensitizers, provides a potentially cheap technique of increasing the radiosensitivity of tumors that can be used with existing radiation therapy equipment without any need to invest in additional equipment.

The largest class of radiosensitizers is the hypoxic cell sensitizers. These pharmaceuticals overcome the radioresistance afforded some tumor cells by their lack of oxygen (hypoxia). Within this class electron-affinic nitroimidazoles have been found in general to radiosensitize hypoxic tumor cells. Two nitroimidazoles, misonidazole and metronidazole, have been deemed suitable for clinical use. "Optimization of Radiotherapy", WHO Technical Report Series 644, World Health Organization, 1980. Misonidazole (hereinafter designated MIS) appears to have the greater radiosensitizing activity of the two compounds. Even so, its clinical applications are limited by its neurotoxicity and a total dose not exceeding 12 g/m$^2$ of body surface is recommended in man. Dische, et al, "Clinical Testing of Radiosensitizer RO 07-0582: Experience with Multiple Doses", Br J Cancer 35, 567–79, 1977. When used at this dose rate with each fraction of a conventional multifraction radiotherapy regime, MIS achieves suboptimal radiosensitization. Thus, there is clearly a need for effective radiosensitizers that are less toxic than MIS.

SUMMARY OF THE INVENTION

The present invention was based on the concept that 2-nitroimidazoles having a lower octanol:water partition coefficient than MIS might have less tendency to cross the blood-brain and blood-nerve barriers but still be able to enter hypoxic cells and radiosensitize them. If this was true, such compounds might be able to be used at doses that maximized radiosensitization of the hypoxic cells but lacked the neurotoxicity associated with MIS because of their relatively low concentration in brain and nerve tissues.

This concept led to the discovery that the partition coefficient of 2-nitroimidazoles is indeed an important parameter as regards radiosensitization and neurotoxicity. In this regard two nitroimidazoles, one being a known compound and the other being novel, were found to have minimum penetration into the brain and nerve tissues combined with maximum penetration into the hypoxic cells in tumors. Surprisingly, their concentration in the tumor cells peaks at a significantly higher concentration than does MIS. This combination of properties—an increased tumor cell concentration and low brain and nerve penetration—is believed to make these two compounds the optimal radiosensitizers of the electron-affinic nitroimidazoles.

The known compound is N-(2-hydroxyethyl)-2-(2-nitro-1-imadazoyl) acetamide. U.S. Pat. No. 3,679,698 discloses it (Example 4) as a species of a genus of 1-substituted 2-nitroimidazoles. While the patent suggests other pharmaceutical uses for the genus, it does not mention radiosensitization. The new compound is N,N-di-(2-hydroxyethyl)-2-(2-nitro-1-imidazolyl) acetamide. It, too, is within the generic formula disclosed by the above mentioned patent. But it is not disclosed specifically.

These two compounds may be represented by the formula:

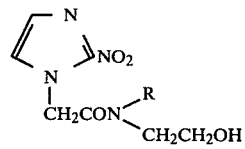

wherein R is hydrogen or a 2-hydroxyethyl radical. The National Cancer Institute has assigned the mono-(hydroxyethyl) compound the code number NSC 301467 and the di-(hydroxyethyl) compound the code number NSC 314055. These two compounds are commonly identified by the code numbers SR-2508 and SR-2555, respectively, in the literature. "Partition Coefficient as a Guide to the Development of Radiosensitizers Which Are Less Toxic than Misonidazole", Brown, J. M. and Workman, P., Radiation Research 82, 171–90, 1980. These compounds will be identified by the latter code numbers hereinafter.

DETAILED DESCRIPTION OF THE INVENTION

Figure 1:
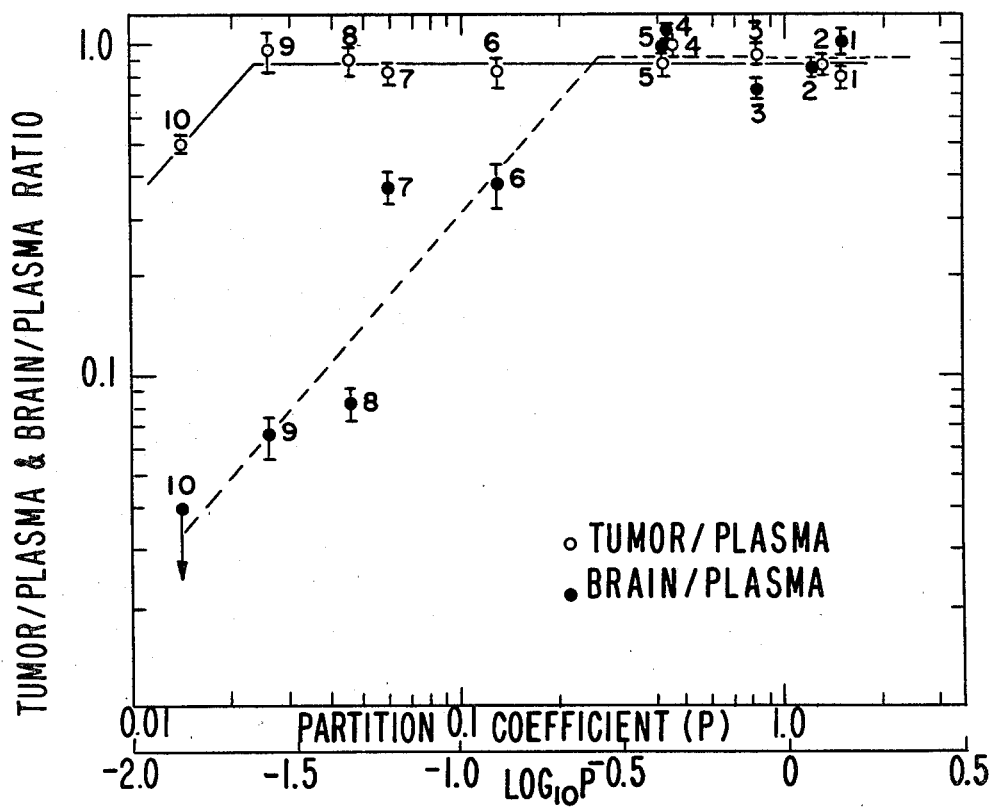
FIG. 1 is a plot of the ratios of concentrations of SR-2508 (compound 8), SR-2555 (compound 9), MIS (compound 5), and seven other 1-substituted 2-nitroimidazoles in the tumor and plasma and brain and plasma versus octanol:water partition coefficient.

SR-2508 and SR-2555 may be prepared by the process described in U.S. Pat. No. 2,679,698 at col. 3, line 68 to col 4, line 64. The following examples illustrates the preparation of these two compounds.

EXAMPLE 1

Preparation of
N-(2-hydroxyethyl)-2-(2-nitro-1-imidazolyl)acetamide
(SR-2508)

The sodium salt of methyl 2-nitroimidazole-1-acetate was formed from 2.20 g (19.5 mmol) of 2-nitroimidazole in 15 ml of N,N-dimethyl-formamide (DMF) and 4.4 ml (19.6 mmol) of 4.45 N sodium methoxide in methanol with heating to 150° C. To the solution at 125° C. was added 1.80 ml or 2.23 g (20.6 mmol) of methyl chloroacetate. The mixture was heated for 15 min at 110°–125° C. and then evaporated to dryness at 50° C., 1.0 mm Hg. The residue was extracted with acetone, filtered and evaporated. Recrystallization of the residue from 50 ml methanol-petroleum ether (30°–60° C.) (3:1) afforded 3.10 g (86%) of methyl 2-nitroimidazole-1-acetate as a white powder, mp 94°–95° C., that was homogeneous by thin layer chromatography on silica gel with diethyl ether ($R_f$ 0.50 with 3 developments). The product was very soluble in ethanol and was soluble in 0.9% saline to the extent of 13.6 mg/ml.

A mixture of 2.50 g (13.5 mmol) of methyl 2-nitroimidazole-1-acetate and 3.0 ml (50.0 mmol) of ethanolamine in 15.0 ml methanol was stirred 20 hr at room temperature. The mixture was diluted with 45 ml ethanol and heated on a stream bath to effect solution. The hot solution was decolorized with charcoal, filtered and evaporated to dryness. The residue was recrystallized from a solution of 150 ml ethyl acetate and 10 ml of methanol to afford 1.81 g (62.4%) of SR-2508 as a white powder, mp 164.5–165.0° C., that was homogeneous by thin layer chromatography on silica gel with 10% methanol in ethyl acetate ($R_f$ 0.16). The solubility of SR-2508 in 0.9% saline solution was approximately 200 mg/ml.

EXAMPLE 2

Preparation of
N,N-di-(2-hydroxyethyl)-2-(2-nitro-1-imidazolyl)acetamide (SR-2555)

A mixture of 4.00 g (21.6 mmol) of methyl 2-nitroimidazole-1-acetate and 4.0 g (38.0 mmol) of diethanolamine in 60.0 ml of methanol was stirred four days at room temperature. After removing the excess diethanolamine, the product was dissolved in 10 ml of methanol and chromatographed through a column of silica gel (70–230 mesh). Elution with 10% methanol in methylene chloride afforded 5.38 g (96%) of product as a hard gum that crystallized after several days to a cream colored hygroscopic solid on silica gel with 20% methanol in methylene chloride ($R_f$ 0.47) and analyzed correctly for $C_9H_{14}N_4O_5$. The solubility of SR-2555 in 0.9% saline solution was over 300 mg/ml.

SR-2508 and SR-2555 possess similar electron affinity and thus similar radiosensitizing efficiency to MIS. They are, however, less lipophilic than MIS. The octanol:water partition coefficients of SR-2508 and SR-2555 are 0.046 and 0.026, respectively, determined using the method of Fujita, et al, J Am Chem Soc 86, 5175, (1964). In comparison MIS has an octanol:water partition coefficient of 0.43. In this regard it is believed that a partition coefficient in the range of about 0.025 to about 0.05 provides the optimum hydrophilic-lipophilic balance for achieving maximum radiosensitization with minimum acute toxicity and neurotoxicity. Electron-affinic 1-substituted 2-nitroimidazoles that are more hydrophilic are poorer radiosensitizers whereas the more lipophilic analogs are more toxic.

Table 1 below reports the molecular weights, partition coefficients, 1-electron reduction potentials, and acute $LD_{50}$ values for ten 1-substituted 2-nitroimidazoles, including SR-2508, SR-2555 and MIS. The LD50 values were obtained in the conventional fashion by administering the test nitroimidazole to BALB/c mice (20–25 g).

TABLE 1

| Compound No | | 1-Substituent structure | Mol wt | Partition coeff (P) | $E_7^1$ (mV) | Acute $LD_{50}$ (mg/g) |
|---|---|---|---|---|---|---|
| 1 | | —CH₂CHOHCH₂Cl | 205 | 1.5 | −384 | ~0.18 |
| 2 | | —CH₂CHOHCH₂OEt | 215 | 1.27 | −391 | >1.1 |
| 3 | |  | 263 | 0.82 | −390 | ~0.9 |
| 4 | | —CH₂CHOHCH₂F | 189 | 0.44 | −383 | ~0.9 |
| 5 | (MIS) | —CH₂CHOHCH₂OMe | 201 | 0.43 | −389 | 1.8(1.3–2.6) |
| 6 | | —CH₂CHOHCH₂OH | 187 | 0.13 | −389 | 3.1(2.2–4.4) |
| 7 | | —CH₂CH₂SOCH₃ | 203 | 0.060 | N.D. | ~2.0 |
| 8 | (SR-2508) | —CH₂CONHCH₂CH₂OH | 214 | 0.046 | −388 | 4.9(4.3–5.6) |
| 9 | (SR-2555) | —CH₂CON(CH₂CH₂OH)₂ | 258 | 0.026 | −398 | >7.7 |
| 10 | | —CH₂CONHCH₂CHOHCH₂OH | 244 | 0.014 | −392 | >6.1 |

Compounds 4–10 of Table 1 were tested for radiosensitization activity by the procedure described by Brown, J M, "Selective Radiosensitization of the Hypoxic Cells of Mouse Tumors with the Nitroimidazoles Metronidazole and RO 7-0582", Radiation Research 64, 633–47 (1975), which description is incorporated herein by reference. At an equal tumor concentration each of the compounds except number 10 was just as effective as MIS in ability to radiosensitize EMT6 tumor cells. Compound 10 was found to be significantly inferior to MIS as a radiosensitizer both for tumors in vivo and cells in vivo, Brown, J M and Lee, W W, Proceedings of Conference on Combined Modality Treatment: Radiation Sensitizers and Protectors, Key Biscayne, 3–6 Oct. 1979. Other investigators have reported that compounds 1–3 have similar radiosensitizing activity to MIS. Adams, et al, Int J Radiation Biol 35, 133–50 (1979) and Rauth, et al, Br J Cancer 37, Suppl III, 202–5 (1978). These results and the $LD_{50}$ data reported in Table 1 show that while SR-2508, SR-2555 and MIS may have comparable radiosensitizing activity, the acute toxicities of SR-2508 and SR-2555 are about three to five times less than that of MIS.

Figure 2:
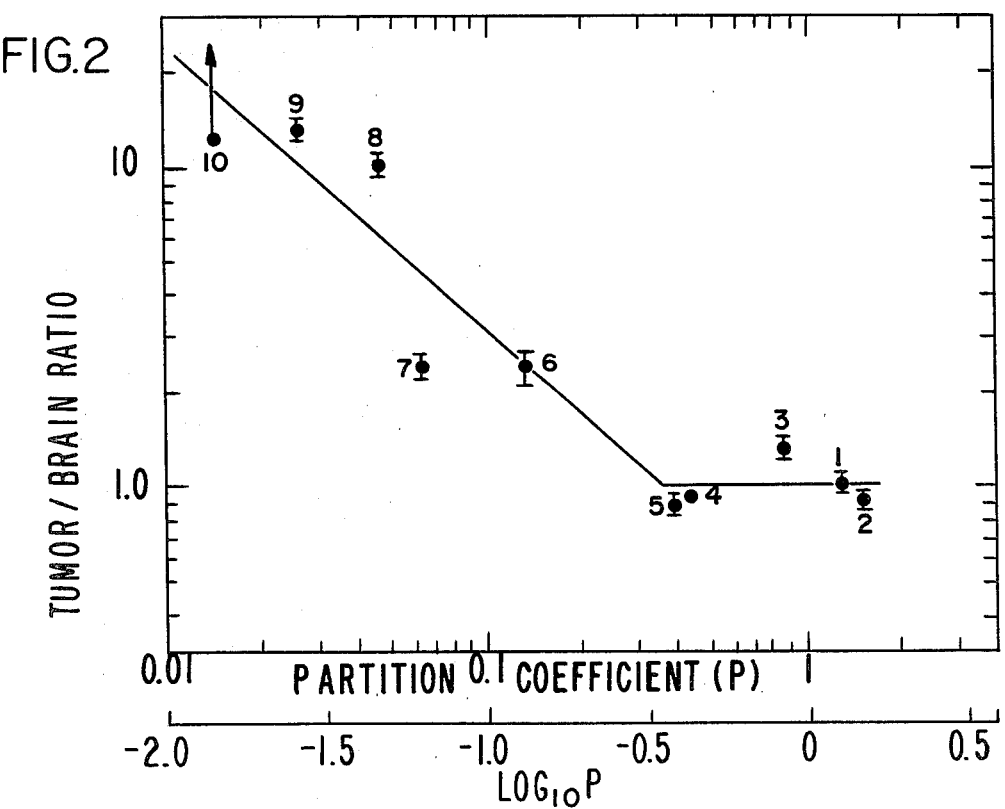
FIG. 2 is a plot of the ratio of concentrations of the same compounds in the tumor and brain versus octanol:water partition coefficient.

The basis for the reduced neurotoxicity of SR-2508 and SR-2555 relative to the other radiosensitizing 2-nitroimidazoles listed in Table 1 is evidenced by the data depicted in FIGS. 1 and 2 and by the fact that neurotoxicity is related to total exposure of neural tissues to the drug. Those data were developed as follows. Adult BALB/c mice (20-25 g) bearing EMT6 tumors were the test animals. Each test compound was formulated immediately before administration to the animals in Hanks' balanced salt solution at a concentration such that the volume injected intraperitoneally was 0.05 ml per g body weight. The doses used were 5 mmole/kg except for compounds 1, 4, and 3 for which the doses were 0.5, 2.5, and 2.0 mmole/kg, respectively.

The mice were injected intraperitoneally and at various times were bled by cardiac puncture under anesthesia. Plasma was obtained by centrifugation and stored frozen at $-20°$ C. The tumor and whole brain were taken immediately after cardiac puncture and stored frozen at $-20°$ C. Plasma and tissue homogenates (20% w/v in distilled water) were analyzed for nitroimidazole concentration by reversed phase high-performance liquid chromatography by the procedure of Workman, et al, J Chromatogr 145, 507-12 (1978) except that the concentration of methanol in the mobile phase was varied from 30% to 50% depending on the column retention times of the individual compounds.

FIG. 1 is a plot of the mean tumor/plasma and brain/plasma ratios ($\pm$1SE) for the ten compounds of Table 1 as a function of their octanol:water partition coefficient. The tumor/plasma ratio for each compound is the mean value from all mice sacrificed at and beyond the time of the peak tumor/plasma ratio observed (from 45 or 75 min depending on the compound). The brain/plasma ratio is the mean value from all the mice for each compound. FIG. 1 shows that at equilibrium all of the compounds have essentially equivalent tumor/plasma ratios. This is additional evidence of the similarity of the radiosensitizing activities of the compounds. On the other hand the brain/plasma ratio shows a marked dependency on lipophilicity at partition coefficients below about 0.4 SR-2508 (compound 8) and SR-2555 (compound 9) have tumor/brain ratios an order of magnitude greater than MIS (compound 5). This evidences that SR-2508 and SR-2555 cross the blood/brain barrier to a lower degree than does MIS and indicates a significant reduction in the potential neurotoxicity of those compounds as compared to MIS. FIG. 2 plots the mean tumor/brain ratio ($\pm$1SE) versus partition coefficient and also shows the favorable distribution of SR-2508 and SR-2555 between the tumor and brain relative to the other nitroimidazole radiosensitizers.

The neurotoxicity of SR-2508 and SR-2555 as compared to MIS was assayed using an accelerated rotarod device by the procedure described in Dunham, N W and Meyer, T S, J Amer Pharm Assn 46, 208-9 (1957) and Conroy, et al, Int J Radiat Oncol Biol Phys 5, 983-91 (1979). Performance and toxicity determinations were made after four-and-one-half weeks of daily dosing. Table 2 reports the results of the above described rotarod tests.

TABLE 2

| Drug | Daily Dose (mg/g) | Performance Relative to Controls | Dose to Give Equivalent Neurotoxicity Relative to MIS |
|---|---|---|---|
| MIS | 0.3 | 1.02 ± 0.18 | 1 |
| MIS | 0.4 | 0.98 ± 0.15 | 1 |
| MIS | 0.5 | 0.94 ± 0.14 | 1 |
| MIS | 0.6 | 0.61 ± 0.12* | 1 |
| MIS | 0.7 | 0.39 ± 0.10** | 1 |
| SR-2508 | 2.0 | 1.10 ± 0.19 | >3.3 |
| SR-2555 | 3.0 | 1.07 ± 0.16 | >5 |

*$0.01 < P < 0.02$
**$P < 0.01$

These results indicate that SR-2508 and SR-2555 are less neurotoxic than MIS by a significant factor (at least a factor of 3-5).

Comparative pharmacokinetic, tumor penetration, and toxicity studies on SR-2508, SR-2555, and MIS were also carried out using the dog as a model. The imidazoles were formulated in a 0.9% sodium chloride solution at a concentration of 5%. Doses of 0.25-1.0 mmole/kg of each compound were administered to normal adult, male cross-bred dogs and subsequent plasma concentrations were monitored by high performance liquid chromatography. Samples of brain, cerebrospinal fluid (CSF), and peripheral nerve (PNS) were removed for assay from similarly dosed dogs over the same test period. Estimates for drug exposure to these fluids/tissues were calculated as the area under the curve (AUC) for the drug concentration-time plot and were standardized for an injected dose of 0.5 mmole/kg. These results are reported in Table 3.

TABLE 3

| Compound | Partition Coefficient P | Plasma Clearance l.kg$^{-1}$hr$^{-1}$ | AUC | | | | Mean Peak Tumor Concentration μmoles.g$^{-1}$ |
|---|---|---|---|---|---|---|---|
| | | | Plasma | Brain | CSF | PNS | |
| | | | μmoles.hr.ml$^{-1}$ or g$^{-1}$ | | | | |
| MIS | 0.43 | 0.09 | 3.68 | 2.32 | 2.66 | 2.25 | 0.56 |
| | | (0.09–0.10) | (2.75–4.83) | (1.26–2.92) | (2.25–3.15) | (1.75–2.75) | (0.43–0.66) |
| SR-2508 | 0.046 | 0.21 | 2.67 | 0.37 | 0.34 | 0.56 | 1.31 |
| | | (0.20–0.22) | (1.98–3.01) | (0.23–0.45) | (0.12–0.42) | (0.23–0.81) | (1.08–2.10) |
| SR-2555 | 0.026 | 0.26 | 1.62 | 0.51 | 0.17 | 0.75 | 1.30 |
| | | (0.23–0.29) | (1.61–1.63) | (0.35–0.68) | (0.08–0.25) | (0.57–0.94) | |

As reported the clearance rates for SR-2508 and SR-2555 were considerably more rapid than for MIS and penetration into brain, CSF and peripheral nerves (PNS) were all considerably lower. As a result of these two factors, total exposure of neural tissues (or AUC) was significantly smaller than for MIS. Table 3 also reports the mean peak tumor concentrations for MIS, SR-2508, and SR-2555 obtained from tests in which these drugs were administered intravenously as bolus injections at a dose of 0.5 micromoles/g to dogs bearing spontaneous tumors. In these tests peak tumor concentrations were reached considerably earlier than MIS and were considerably higher than MIS. The data of Table 3 indicate SR-2508 and SR-2555 are likely to be more effective radiosensitizers than MIS since this depends on peak tumor concentration, and are also likely to be much less neurotoxic since this depends on AUC for neural tissues.

The above tests show that SR-2508 and SR-2555 may be used to radiosensitize hypoxic tumor cells in warm-blooded hosts with reduced neurotoxicity relative to MIS. Because of the similarity between the lipid membranes that form the blood/tissue barriers in the different species of warm-blooded animals, SR-2508 and SR-2555 will exhibit similar activity in species of warm-blooded animals other than those tested above. Such other species include humans and other primates, avians, farm animals such as cattle, sheep and pigs, and sports animals and pets such as horses and cats.

Hypoxia is believed to be associated with all types of solid malignant neoplasms. The invention may, therefore, be used to treat neoplastic epithelial cells, endothelial cells, connective tissue cells, bone cells, muscle cells, nerve cells, and brain cells. Examples of carcinomas and sarcomas that may be radiosensitized include carcinomas such as epithelial cell, acinic cell, alveolar cell, basal cell, basal squamous cell, cervical, renal, liver, Hurthle, Lucké, mucinous and Walker, and sarcomas such as Abernathy's, alveolar soft part, angiolithic, botyroid, encephaloid, endometrial stroma, Ewing's, fascicular, giant cell, lymphatic, Jensen's, juxtacortical osteogenic, Kaposi's, medularry, and synovial. Other specific examples of tumors that have been radiosensitized with 1-substituted 2-nitroimidazoles are reported by Adams, G E, Hypoxic cell radiosensitizers for radiotherapy. In *Cancer: A Comprehensive Treatise* (F Becker, Ed), Vol 6, pp 181-223, Plenum, New York, 1977.

The compounds may be administered to the animals orally or parenterally (intravenously, subcutaneously, intramuscularly, intraspinally, intraperitoneally, and the like). It is likely, however, that the preferred route will be intravenous. When administered parenterally they will normally be formulated in a unit dosage injectable form (solution, suspension, emulsion) with a pharmaceutically acceptable vehicle. Such vehicles are typically nontoxic and nontherapeutic. Examples of such vehicles are water, aqueous vehicles such as saline, Ringer's solution, dextrose solution, and Hanks' solution and nonaqueous vehicles such as fixed oils (such as corn, cottonseed, peanut, and sesame), ethyl oleate, and isopropyl myristate. Sterile saline is a preferred vehicle and the compounds are sufficiently soluble to be made up as a solution for all forseeable needs. The vehicle may contain minor amounts of additives such as substances that enhance solubility, isotonicity, and chemical stability, e.g., antioxidants, buffers, and preservatives. When administered orally the compounds will usually be formulated into a unit dosage form such as a tablet, capsule, suppository or cachet. Such formulations typically include a solid, semisolid or liquid carrier or diluent. Exemplary diluents and vehicles are lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan monolaurate, methyl hydroxybenzoate, propylhydroxybenzoate, talc, and magnesium stearate.

The amount of drug administered to the host animal is sufficient to radiosensitize the malignant neoplasm to be treated but below that which may elicit toxic effects. Said amount will depend upon the type of tumor, the animal species and the weight or body surface of the animal. For example, the above tests indicate that for treating tumor bearing mice about 0.5 to about 5 mmol/kg would be administered while for dogs about 0.2 to 2.5 mmol/kg would be given. The compounds may be administered to humans in a variety of different fractionation regimes, with dosages varying from 0.5 to 20 g/m$^2$, depending upon the regime. These are likely to vary from intravenous daily (ie, five times per week) doses for up to six weeks, to once weekly intravenous doses for four to six weeks with the total dose not exceeding about 120 g/m$^2$. Individual doses for the once weekly fractionation regimen are likely to be in the range of 2 to 20 g/m$^2$ and usually in the range of 5 to 15 g/m$^2$. Individual doses for the daily or five times per week fractionation regime are likely to be in the range of 0.5 to 5 g/m$^2$. For intermediate fractionation regimes (eg, two or three fractions per week for four to six weeks) individual doses would be between these two limits. Since tumor concentration of drug is directly related to radiosensitivity, the drugs will ideally be administered at a time such that the peak concentration of drug in the hypoxic cells occurs at the time the tumor is exposed to radiation. This time will depend upon the manner in which the drug is administered, the particular dosage form employed, the type of tumor, and the species of host animal. The above reported mouse and dog studies indicate that intravenous administration about ½ to about 1 hr prior to radiation exposure may provide maximum radiosensitization. Oral administration may require a somewhat longer lag because the drug must first pass through the gastrointestinal barrier. In view of this prodrug forms of the nitroimidazoles that pass through the gastrointestinal barrier into circulation rapidly and then quickly convert to SR-2508 and SR-2555, as the case may be, may be used to enhance the effectiveness of oral administration. For instance the acetate esters of SR-2508 and SR-2555 were prepared and had partition coefficients of 0.13 and 0.23, respectively. SR-2508, SR-2555 and their acetate esters were administered to mice orally at 4 or 5 mmole/kg, and plasma concentrations were monitored by the above described techniques. The peak concentrations in the plasma of SR-2508 or SR-2555 were significantly higher following oral administration of their esters than following oral administration of the parent drugs. In the case of SR-2555 the peak concentration was ten-fold higher after prodrug administration than it was after oral administration of SR-2555 itself.

Modifications of the above described compounds, compositions, and processes that are apparent to those of skill in the chemical, pharmaceutical, and related arts are intended to be within the scope of the following claims.

We claim:

1. Method of radiosensitizing hypoxic tumor cells in a warm-blooded animal with reduced neurotoxic side effects comprising administering a compound of the formula

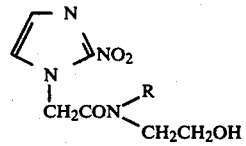

wherein R is hydrogen or a 2-hydroxyethyl radical to the animal systemically at a dosage level that radiosensitizes said cells.

2. The method of claim 1 wherein the animal is a human, the administration is intravenous and in a fractionation regime with the total dose not exceeding about 120 g/m².

3. The method of claim 2 wherein the regime is weekly doses for up to six weeks and the individual dose is in the range of about 2 to about 20 g/m².

4. The method of claim 2 wherein the regime is daily doses for up to six weeks and the individual doses are in the range of about 0.5 to about 5 g/m².

5. The method of claim 2 or claim 3 wherein the compound is administered intravenously about one-half to about one hour before said cells are exposed to radiation.

6. The method of claim 1 wherein the administration is oral and the compound is in the form of a prodrug that passes through the gastrointestinal barrier of the animal more rapidly than the compound and converts to the compound once in the circulatory system of the animal, and wherein the prodrug is the acetate ester of the compound.

* * * * *